United States Patent
Soru et al.

(10) Patent No.: US 9,827,371 B2
(45) Date of Patent: Nov. 28, 2017

(54) METHOD FOR CONTROLLING THE DELIVERY OF INSULIN AND THE RELATED SYSTEM

(75) Inventors: Paola Soru, Pavia (IT); Lalo Magni, Pavia (IT); Chiara Toffanin, Pavia (IT); Giuseppe De Nicolao, Milan (IT); Chiara Dalla Man, Venice (IT); Claudio Cobelli, Padua (IT)

(73) Assignees: DIPARTIMENTO DI INGEGNERIA CIVILE E ARCHITETTURA DELL'UNIVERSITA' DEGLI STUDI DI PAVIA, Pavia (IT); UNIVERSITA' DEGLI STUDI DI PADOVA, Padua (IT)

( * ) Notice: Subject to any disclaimer, the term of this patent is extended or adjusted under 35 U.S.C. 154(b) by 301 days.

(21) Appl. No.: 14/389,936

(22) PCT Filed: Mar. 23, 2012

(86) PCT No.: PCT/IT2012/000083
§ 371 (c)(1),
(2), (4) Date: Mar. 6, 2015

(87) PCT Pub. No.: WO2013/140423
PCT Pub. Date: Sep. 26, 2013

(65) Prior Publication Data
US 2015/0174322 A1 Jun. 25, 2015

(51) Int. Cl.
*A61B 5/145* (2006.01)
*A61M 5/172* (2006.01)
(Continued)

(52) U.S. Cl.
CPC ...... *A61M 5/1723* (2013.01); *A61M 5/14276* (2013.01); *G06F 19/3456* (2013.01);
(Continued)

(58) Field of Classification Search
CPC ...... A61M 5/1723; A61M 2005/14208; A61M 2205/50; A61M 2205/52; G06F 19/3468
(Continued)

(56) References Cited

U.S. PATENT DOCUMENTS

2003/0055570 A1* 3/2003 Ribeiro ............... G06F 19/3468
702/19
2005/0049179 A1* 3/2005 Davidson ............... A61K 38/28
703/11
(Continued)

OTHER PUBLICATIONS

International Search Report for corresponding International Patent Application No. PCT/IT2012/000083 mailed Dec. 12, 2012.
(Continued)

*Primary Examiner* — Gerald Landry, II
(74) *Attorney, Agent, or Firm* — Merchant & Gould P.C.

(57) ABSTRACT

A method (400) controls the delivery of insulin in a diabetic patient (P) based on data (d) representative of at least a fraction of a meal (m(k+i)) that the patient (P) will consume. The method provides from a block (R) representative of conventional therapy or open loop rule that the patient (P) is subject to, based on the data (d) representative of at least a fraction of the meal (m(k+i)), a reference insulin value ($u_0$). The method is also based on data representative of the difference between input data (ŷ), a reference glycemic level, and feedback data ($y^{CGM}$) representative of the glycemic level detected in the patient (P). A control module (301; 401) provides a value of insulin (i) to be delivered to the patient (P) based on the various representative data.

6 Claims, 5 Drawing Sheets

(51) Int. Cl.
*A61M 5/142* (2006.01)
*G06F 19/00* (2011.01)

(52) U.S. Cl.
CPC .................... *G06F 19/3468* (2013.01); *A61M 2005/14208* (2013.01); *A61M 2205/04* (2013.01); *G06F 19/345* (2013.01)

(58) Field of Classification Search
USPC .......................... 604/65–67, 131–155, 890.1
See application file for complete search history.

(56) References Cited

U.S. PATENT DOCUMENTS

| | | | | |
|---|---|---|---|---|
| 2007/0179434 A1* | 8/2007 | Weinert | ................ | G06F 9/4443 604/66 |
| 2008/0147050 A1* | 6/2008 | Mann | ................ | A61M 5/14244 604/890.1 |
| 2008/0183060 A1* | 7/2008 | Steil | ................... | A61B 5/14532 600/365 |
| 2008/0206799 A1* | 8/2008 | Blomquist | .......... | G06F 19/3456 435/14 |
| 2009/0006133 A1* | 1/2009 | Weinert | ............. | A61B 5/14532 705/3 |
| 2009/0018406 A1* | 1/2009 | Yodfat | ................. | A61B 5/0002 514/1.1 |
| 2011/0098548 A1* | 4/2011 | Budiman | ............ | G06F 19/3437 600/365 |
| 2011/0130746 A1* | 6/2011 | Budiman | ........... | A61B 5/14532 604/890.1 |
| 2012/0059353 A1* | 3/2012 | Kovatchev | .......... | G06F 19/3437 604/504 |
| 2012/0123234 A1* | 5/2012 | Atlas | .................... | A61B 5/7264 600/365 |
| 2012/0245556 A1* | 9/2012 | Kovatchev | ......... | A61B 5/14532 604/504 |
| 2013/0211220 A1* | 8/2013 | Cobelli | ................ | A61B 5/7275 600/365 |

OTHER PUBLICATIONS

Garcia-Gabin et al., "Robust Sliding Mode Closed-loop Glucose Control with Meal Compensation in Type 1 Diabetes Mellitus", Proceedings of the 17$^{th}$ World Congress the International Federation of Automatic Control, vol. 17, Jan. 1, 2008, pp. 4240-4245.

Marchetti et al., "A feedforward-feedback glucose control strategy for type 1 diabets mellitus", Journal of Process Control, vol. 18, 2008, pp. 149-162.

Hovorka et al., "Closing the Loop: The Adicol Experience", Diabetes Technology & Therapeutics, vol. 6, No. 3, Jun. 1, 2004, pp. 307-318.

Abu-Rmileh et al., "A robust sliding mode controller with internal model for closed-loop artificial pancreas", Medical & Biological Engineering & Computing, vol. 48, No. 12, Jul. 24, 2010, pp. 1191-1201.

Lynch et al., "Model predictive control of blood glucose in type I diabetics using subcutaneous glucose measurements", Proceedings of the 2002 American Control Conference, vol. 5, May 8, 2002, pp. 4039-4043.

* cited by examiner

METHOD FOR CONTROLLING THE DELIVERY OF INSULIN AND THE RELATED SYSTEM

This application is a National Stage Application of PCT/IT2012/000083, filed 23 Mar. 2012, and which application is incorporated herein by reference. To the extent appropriate, a claim of priority is made to the above disclosed application.

BACKGROUND OF THE INVENTION

The present invention refers to insulin therapy techniques for diabetic patients and in particular to a method for controlling the delivery of insulin in diabetic patients and to the related system.

Diabetes is a pathology that involves glycemic regulation and it can be divided into two types or categories: type 1, or insulin dependent, and type 2, or insulin resistant.

The first category (type 1) is characterised by the destruction of beta cells in the pancreas, responsible for the production of insulin, and consequently by the complete dependency of patients on delivering of insulin from the outside.

The second category (type 2) is characterised by an alteration in the secretion of insulin and a reduction in sensitivity to such a hormone.

Adequate glycemic regulation, with levels contained within a glycemic range equal to 70-140 mg/dl, is of primary importance for both categories of diabetes since a low level of glycemia in the blood, hypoglycemia, can take the diabetic patient into a coma and, if not appropriately treated, death. On the other hand, a high level of glycemia in the blood, hyperglycemia, over a long period can lead to long-term problems, including cardiovascular illnesses, ictus, hypertension, retinopathy, renal complications and alterations of various types to the nervous system.

Currently, scientific research is of course aimed at preventing the spread of the pathology and at optimising insulin therapy techniques by developing methods and systems for controlling the delivery of insulin in a diabetic patient, in order to regulate the level of glycemia in the blood of the patient.

Currently in development is a system for automatically controlling the delivery of insulin in a diabetic patient, defined in the literature as "artificial pancreas", consisting of a subcutaneous glycemia sensor and a subcutaneous insulin pump implanted in the patient, connected to a microcontroller configured to carry out, through the execution of a suitable algorithm, a method for controlling the delivery of insulin in the patient.

SUMMARY OF THE INVENTION

As stated earlier, the objective of a method for controlling the delivery of insulin is that of keeping the level of glycemia in the blood within an optimal range of values, typically 70-140 mg/dl.

As can easily be observed, the definition of the aforementioned control method is very complex since it needs to take into account different critical aspects such as the presence, for example, of time-variable dynamics, of non-linear phenomena and of time delays both in the absorption of insulin from the subcutaneous level to the blood and, contrarily, in the absorption of glucose from the blood to the subcutaneous level.

Moreover, the level of glycemia in the blood depends on the insulin value delivered in the patient, typically comprised between a minimum value equal to zero and a maximum value set by the subcutaneous insulin pump, but also on other disturbances to be taken into consideration like, for example, the meals consumed or the physical activity carried out by the patient.

Regarding this, an essential aspect to be taken into consideration in the definition of the method for controlling the subcutaneous delivery of insulin in a diabetic patient is the need to compensate, above all, the effects due to the meals consumed by the patient.

Indeed, whilst, on the one hand, night-time glycemia control is a problem with standard regulation in which a constant or slightly time-variable glycemic set-point must be followed, on the other hand, the meals consumed by the patient produce rapid excursions of the glycemic values that can only be managed by delivering the necessary insulin in a relatively brief time window.

In order to manage this critical situation, conventional insulin therapy for patients equipped with a subcutaneous pump foresees the delivery of a flow of insulin, called "basal", typically constant in portions, delivered throughout the day. The compensation of meals, on the other hand, is obtained through "impulsive" delivery of large quantities of insulin, also called pre-meal bolus, delivered to the patient through the pump in combination with the meals and determined based on the amount of carbohydrates ingested. Some subcutaneous pumps allow the pre-meal bolus to be determined also using information on the current glycemic level and on possible boluses given previously (for example corrective boluses delivered to correct episodes of hyperglycemia).

A method for controlling the delivery of insulin, of the "artificial pancreas" type, already clinically tested by various centres of research, can be described with reference to the block diagram of FIG. 1.

The control method of FIG. 1 is based on a known approach for controlling the delivery of insulin, i.e. predictive control MPC (Model Predictive Control).

The block diagram of FIG. 1 comprises an actuation path PA and a feedback or closed loop path PR.

The actuation path PA comprises a first computing node C1, a linear model predictive controller 100 LMPC, a second computing node C2 and a block P representative of the patient.

The first computing node C1 is suitable for providing the predictive controller 100, at a moment in time k, with data representative of the difference between input data ŷ, representative of a reference glycemic level, and feedback data $y^{CGM}$, representative of the subcutaneous glycemic level detected in the patient P at a previous moment in time. The feedback data $y^{CGM}$ is obtained through a sensor that continuously measures the glycemic level in the subcutaneous tissue of the patient P (Continuous Glucose Monitoring, CGM).

The predictive controller 100, based on the data representative of the difference between the input data ŷ, representative of the reference glycemic level, and the feedback data $y^{CGM}$, representative of the concentration level of glucose detected in the subcutaneous tissue of the patient P, and based on data m̂(k+i), representative of the foreseen meal that the patient P will ingest at the time k+i, is suitable for providing data $u^{MPC}$, representative of a corrective insulin value.

The second computing node C2 is suitable for providing the amount i of insulin to be delivered to the patient P, as the sum of the data $u^{MPC}$ representative of the corrective insulin value, and of a basal insulin value $u_b$, known for every patient since it is part of conventional therapy. The patient eats the meals indicated in the diagram with m.

The control method represented by the diagram of FIG. 1 controls the delivery of insulin to the patient P automatically combining the actions along the feedback path PR and along the actuation path PA.

However, the physiological delays of the patient-system, the saturation limits of the subcutaneous pump for delivery of insulin and the lack of a reliable individual model of the patient impose intrinsic limits to the time constant that can be obtained by the system in feedback, so that the stability of the system in closed loop necessary to avoid events of hyperglycemia in the blood of the patient is ensured.

In order to overcome this problem, a further method for controlling the delivery of insulin in a diabetic patient has been developed, which does not combine, but rather divides, the actions that are carried out, respectively, over the feedback path and over the compensation path of the meals in an open loop.

Such a further control method can be described with reference to the block diagram of FIG. 2.

The block diagram of FIG. 2 also comprises an actuation path PA and a feedback path PR in a closed loop.

The block diagram of FIG. 2 also comprises a compensation path in an open loop POL that also acts over the actuation path PA.

The actuation path PA comprises a first computing node C1, a second computing node C2, a linear model predictive controller 200 LMPC, a third computing node C3, a block P, representative of the patient-system, and feedback data $y^{CGM}$, representative of the glycemic level detected in the patient P at a previous moment k, that, through the feedback path PR in a closed loop, connects the patient-system P to the second computing node C2.

The first computing node C1 is suitable for providing the second computing node C2 with data $\tilde{y}$, representative of the reference glycemic level as the sum between data $y_r$, representative of the reference glycemic level in the absence of meals, and data $\hat{y}$, representative of a foreseen variation in the expected glycemic level due to the expected meal, provided by the compensation path in an open loop POL.

The second computing node C2 is suitable for providing the predictive controller 200, at a moment in time k, with data representative of the difference between the data $\tilde{y}$, representative of a reference glycemic level, and the feedback data $y^{CGM}$, representative of the subcutaneous glycemic level detected in the patient P at a previous moment in time. The feedback data $y^{CGM}$ is obtained through continuous monitoring of the glycemic level of the subcutaneous tissue of the patient P (Continuous Glucose Monitoring, CGM).

The predictive controller 200, based on the data representative of the difference between the input data $\tilde{y}$, representative of the reference glycemic level and the feedback data $y^{CGM}$, representative of the glycemic level detected in the patient P, is suitable for providing data $u^{MPC}$ representative of a first insulin variation value with respect to a basal insulin value.

The third computing node C3 is suitable for providing the quantity i of insulin to be delivered to the patient P, as the sum from the data $u^{MPC}$ representative of the first insulin variation value with respect to the basal insulin value, of a basal insulin value $u_b$ and of a second insulin variation value $u_c$ provided by the compensation path in an open loop POL. The patient eats meals indicated in the diagram with m.

The compensation path in an open loop POL comprises a block R, representative of a method for calculating the pre-meal boluses $u_c$ according to a conventional therapy to which the patient P is subjected, which is suitable for providing, based on data $\hat{m}(k+i)$, representative of the foreseen meal that the patient P will consume at the time k, the second insulin variation value $u_c$ both to the third computing node C3 and to an empirical model ME of the compensation path in an open loop POL.

The empirical model ME is suitable for providing, based on the data $\hat{m}(k+i)$, representative of the foreseen meal that the patient P will consume at the time k+i, and of the second insulin variation value $u_c$, the data $\hat{y}$, representative of the foreseen variation in the expected glycemic level, due to a part of the expected meal, to the first computing node C1 of the actuation path PA.

The further control method represented by the diagram of FIG. 2 has the advantage of incorporating individual knowledge integrated in well-established therapeutic practice, but it still has various drawbacks.

Indeed, the pre-meal boluses $u_c$ are essentially established according to static and empirical rules and are released without taking into account, in real time, the historical information relative to the feedback data $y^{CGM}$ and to the insulin released before.

Another drawback is due to the fact that, in order to provide an approximation of the data $\hat{y}$, representative of the foreseen variation in the expected glycemic level due to a part of the expected meal, based on the second insulin variation value $u_c$, a "rough" and empirical patient model is used that can be an obstacle to acceptable predictions.

The purpose of the present invention is to devise and provide a method for controlling the delivery of insulin in a diabetic patient that makes it possible to at least partially avoid the aforementioned drawbacks with reference to the prior art and that is able to also ensure greater robustness with respect to it.

Such a purpose is accomplished through a method for controlling the delivery of insulin.

The object of the present invention is also a system for controlling the delivery of insulin.

The object of the present invention is also a programme product.

BRIEF DESCRIPTION OF THE DRAWINGS

Further characteristics and advantages of the control method according to the invention will become clearer from the following description of preferred embodiments, given for indicating and not limiting purposes, with reference to the attached figures, in which.

DETAILED DESCRIPTION OF THE PREFERRED EMBODIMENT

Figure 5:
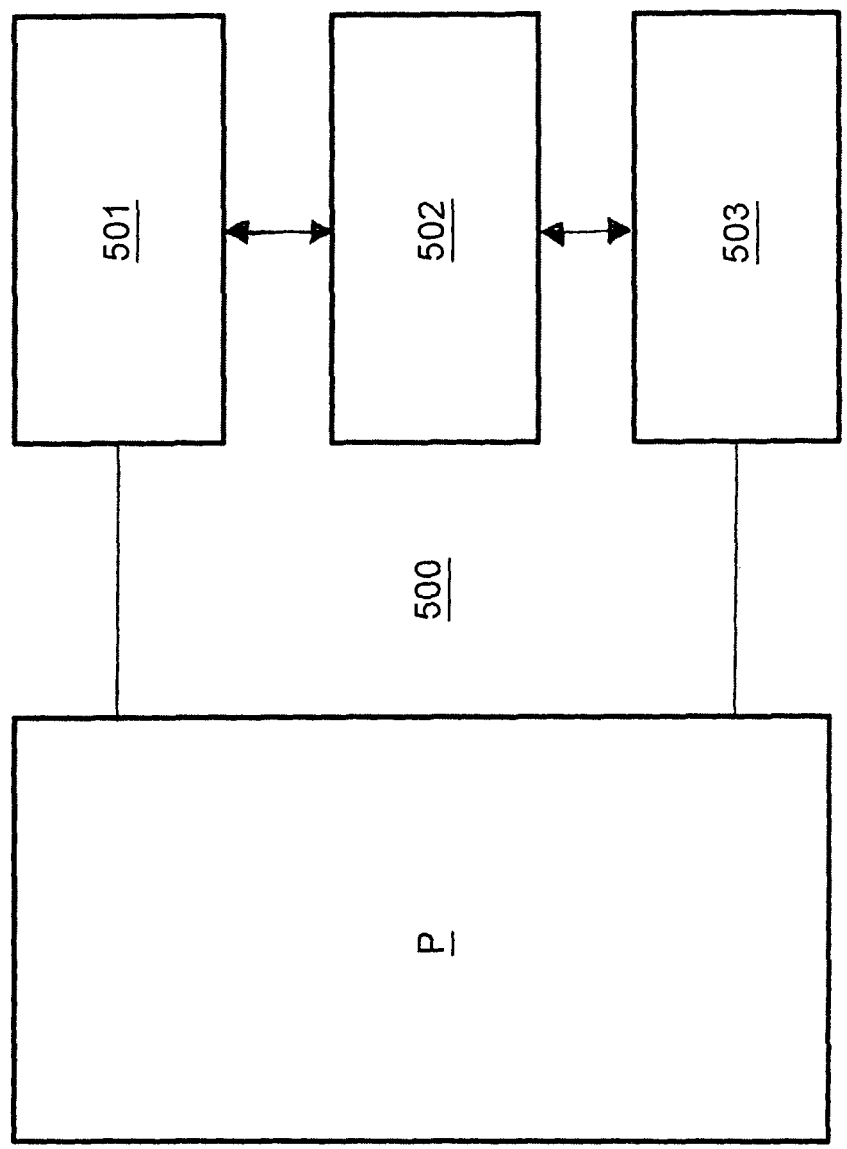
FIG. 5 schematically illustrates through a block diagram a system for controlling the delivery of insulin in a diabetic patient suitable for implementing the control method according to the embodiment of FIG. 3 or the embodiment of FIG. 4.

With reference to FIG. 5, a system for controlling the delivery of insulin, wholly indicated with reference numeral 500, in a diabetic patient P comprises a subcutaneous sensor 501 of the glycemic level of the blood of the patient P suitable for carrying out continuous monitoring of the glycemic level of the blood of the patient P to detect data CGM representative of the glycemic level in the subcutaneous tissue of the patient P.

The control system 500 also comprises a microcontroller 502, for example a microprocessor, operatively connected to the subcutaneous sensor 501 to receive from it the data CGM representative of the glycemic level in the subcutaneous tissue of the patient P detected.

The control system 500 also comprises a subcutaneous pump 503 suitable for delivering to the patient P a set amount of insulin i. The set amount of insulin i to be delivered to the patient P is determined by the microcontroller 502 configured, as will also be repeated hereafter, to implement the method for controlling the delivery of insulin according to the present invention.

Regarding this, the microcontroller 502 is suitable for executing a programme product able to be loaded in a memory unit (not shown in FIG. 5), operatively associated with the microcontroller 502, to allow the microcontroller 502 to carry out the control method of the invention.

Now returning to FIG. 3, the block diagram corresponding to the method 300 for controlling the delivery of insulin, hereafter also simply called control method 300, according to a first embodiment, is described.

The block diagram comprises an actuation path P1, a feedback path P2 in a closed loop and a compensation path P3 in an open loop.

The actuation path P1 comprises a first computing node C1, a control module 301, a second computing node C2 and a block P representative of the patient-system.

The first computing node C1 is suitable for providing the control module 301, at a moment in time k, with data representative of the difference between input data $\tilde{y}$, representative of a reference glycemic level, and feedback data $y^{CGM}$, representative of the glycemic level detected in the patient P, at a previous moment k, from the subcutaneous sensor 501. The feedback data $y^{CGM}$ is obtained through continuous monitoring of the glycemic level in the subcutaneous tissue of the patient P (Continuous Glucose Monitoring, CGM).

The compensation path in an open loop P3 is suitable for also providing the control module 301 with data d representative of at least a fraction of a foreseen meal $\hat{m}(k+i)$ that the patient P can consume.

Figure 3:
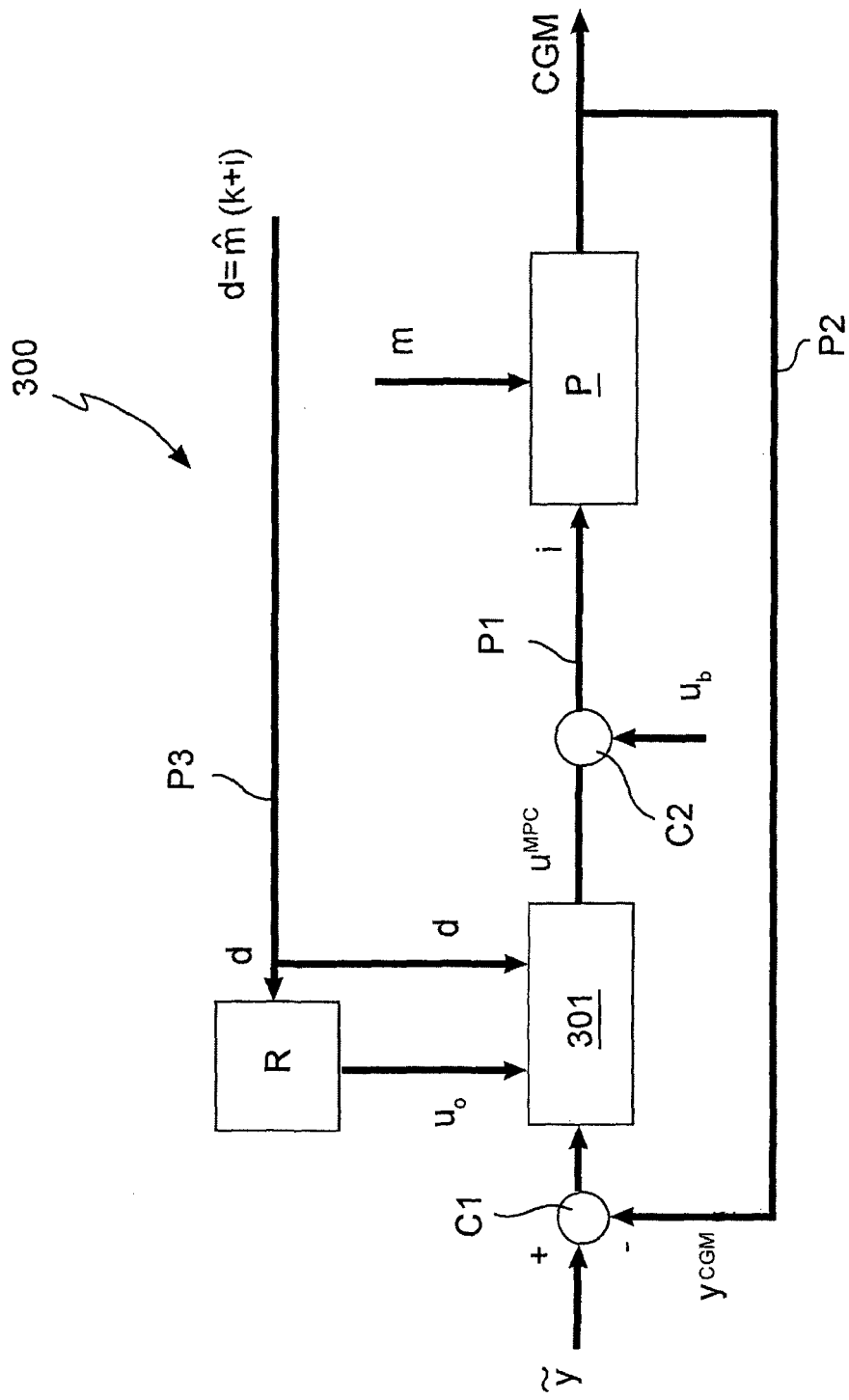
FIG. 3 schematically illustrates through a block diagram a method for controlling the delivery of insulin according to an embodiment of the invention.

It should be observed that in the embodiment illustrated in FIG. 3, the data d is representative of the entire foreseen meal that the patient P can consume.

It should also be noted that the foreseen meal $\hat{m}(k+i)$ can be provided by the patient P or by an automatic prediction module (not shown in the figures).

The compensation path in an open loop P3 comprises a block R, representative of conventional therapy or open loop rule to which the patient P is subject, suitable for providing, based on the data d representative of at least a fraction of the foreseen meal $\hat{m}(k+i)$ that the patient P will consume at the time k+i, a reference insulin value $u_o$ to the control module 301.

The control module 301, based on the data representative of the difference between the input data $\tilde{y}$ representative of the reference glycemic level, and the feedback data $y^{CGM}$, representative of the glycemic level detected in the patient P, and the data d representative of at least a fraction of the foreseen meal $\hat{m}(k+i)$ to be delivered to the patient P at the time k+i, is suitable for providing data $u^{MPC}$, representative of a first insulin variation value.

The control module 301 is, for example, a linear model predictive controller LMPC that uses a linear discrete time model to predict future output data (subcutaneous glycemia detected by the subcutaneous sensor 501) as a function of an input (insulin delivered subcutaneously) and a disturbance (consumption of a meal). The model can be represented by the following linear system:

$$\begin{cases} x(k+1) = Ax(k) + Bu(k) + Md(k) \\ y(k) = Cx(k) \end{cases} \quad (1)$$

in which $x(k) \in R^n$, is the state of the patient-system;

$y(k) = CGM(k) - G_b$(mg/dl), is the difference between the subcutaneous glycemia detected by the subcutaneous sensor 501 and a basal value $G_b$;

$u(k) = i(k) - u_b(k)$(pmol/kg), is the difference between the insulin delivered through the subcutaneous pump 503 and its basal value $u_b$, which can be time-variant. The insulin is normalised to the weight of the patient P;

d(k)(mg), represents the foreseen meal.

Moreover, it is presumed that the set of three parameters A, B, C can be fixed and detected.

The control module LMPC is configured to predict the future glycemic profile knowing the carbohydrates and insulin taken by the patient P. Based on this prediction it is possible to calculate the optimal profile from the future insulin to be delivered, in accordance with the following cost function:

$$J(x(k), u(\cdot), k) = \sum_{i=0}^{N-1} (q(y(k+i) - y_o(k+i))^2 + (u(k+i) - u_o(k+i))^2) + \|x(k+N)\|_P^2 \quad (2)$$

in which q is a positive scalar coefficient that is regulated by the user, N is the prediction horizon.

Moreover, $\|x(k+N)\|_P^2 = x(x(k+N)'Px(k+N)$, in which P is a non-negative matrix, for example, the stabilizing solution of the discrete-time Riccati equation $P=A'PA+qC'C-A'PB(1-B'PB)B'PA$ and $y_o(k) = \tilde{y}(k) - G_b$(mg/dl), is the difference between the reference subcutaneous glycemic value $\tilde{y}$ and the basal value $(G_b)$;

$u_o(t)$ is the reference insulin value provided by R to the control module 301 (corresponding to the control module 401, described hereafter).

In order to avoid on-line optimisation or an additional burden both for the memory space occupied and in terms of computing as a consequence of the use of an explicit predictive controller designed to manage constraints, the design of the control method of the invention does not take into account the possible constraints. Therefore, it is possible to calculate the solution in closed form through the Lagrange formula. In particular, the vector of the predictions $Y(k)=[y(k+1) \ldots y(k+N-1)x(k+N)]'$ can be written as a function of the initial state x(k), of the vector of future insulin delivery $$U(k)=[u(k) \ldots u(k+N-2)u(k+N-1)]'$$

and of the vector of future meals $$D(k)=[d(k) \ldots d(k+N-2)d(k+N-1)]'$$

in the following way:

$$Y(k) = A_c x(k) + B_c U(k) + M_c D(k) \quad (3)$$

in which $$A_c = [CA \ldots CA^{N-1} A^N]'$$

$$B_c = \begin{bmatrix} CB & 0 & \ldots & 0 \\ CAB & CB & \ldots & 0 \\ \ldots & \ldots & \ldots & \ldots \\ CA^{N-2}B & CA^{N-3}B & \ldots & 0 \\ A^{N-1}B & A^{N-2}B & \ldots & B \end{bmatrix} \quad (4)$$

$$M_c = \begin{bmatrix} CM & 0 & \ldots & 0 \\ CAM & CM & \ldots & 0 \\ \ldots & \ldots & \ldots & \ldots \\ CA^{N-2}M & CA^{N-3}M & \ldots & 0 \\ A^{N-1}M & A^{N-2}M & \ldots & M \end{bmatrix}$$

Defining the matrix:

$$Q = \begin{bmatrix} q & 0 & \ldots & 0 & 0 \\ 0 & q & \ldots & 0 & 0 \\ \vdots & \vdots & \ddots & \vdots & \vdots \\ 0 & 0 & \ldots & q & 0 \\ 0 & 0 & \ldots & 0 & q \end{bmatrix} \quad (5)$$

And the reference vectors $$Y_o(k)=[y_o(k+1) \ldots y_o(k+N-1)0]' \in R^{1\times(N-1+n)}$$

$$U_o(k)=[u_o(k+1) \ldots u_o(k+N-2)u_o(K+N-1)]' \quad (6)$$

the cost in (2) can be replaced by $$J(x(k), u(\cdot), k) = (A_c x(k) + B_c U(k) + M_c D(k) - Y_o(k))' \quad (7)$$
$$Q(A_c x(k) + B_c U(k) + M_c D(k) - Y_o(k)) +$$
$$(U(k) - U_o(k))'(U(k) - U_o(k))$$

It should be noted that the term $qy^2(k)$ has been omitted: indeed, it does not influence the solution of the optimisation problem since it does not depend on $u(k+j)$, $j\geq 0$. Zeroing the gradient, the vector of the future optimal in inputs is as follows:

$$U^o(k)=(B'_c QB_c+R)^{-1}(-B'_c QA_c x(k)-B'_c QM_c D(k)+B'_c QY_o(k)+RU_o(k)) \quad (8)$$

which depends on the state at time k, on the future reference values of the control and output variables and on the vector of future meals D(k).

According to the principle of the Receding Horizon, the time invariant control law of the control module LMPC is given by:

$$u^{MPC}(k)=[1 \ 0 \ \ldots \ 0](-K_x x(k)-K_d D(k)+K_{Y_o}Y_o(k)+K_{U_o}U_o(k))). \quad (9)$$

in which the gains are:

$$K_x=(B'_c QB_c+I)^{-1}B'_c QA_c$$

$$K_d=(B'_c QB_c+I)^{-1}B'_c QM_c$$

$$K_{Y_o}=(B'_c QB_c+I)^{-1}B'_c Q$$

$$K_{U_o}=(B'_c QB_c+I)^{-1}$$

The state x(k) of the model is not in general measurable. In order to work around this problem, in the past it has been proposed to use a non-minimum embodiment in state space of the input-output model, the state of which consists of the past input and output values.

However, since only noisy measurements of the output are available (subcutaneous glycemic concentration) the impact of the noise of the subcutaneous sensor on the closed loop performance can be very negative. Therefore, it is foreseen in addition to use a predictor model, for example a Kalman filter, inside the control module 301 (correspondingly, also inside the control module 401 that will be described hereafter with reference to FIG. 4) which, by exploiting the knowledge included in the control module 301 and the insulin delivered in the past, takes care of improving the quality of the information transmitted by the sensor to the control method of the invention.

In order to configure the Kalman filter, noises are introduced in the linear model (1):

$$\begin{cases} x(k+1) = Ax(k) + Bu(k) + Md(k) + v_x(k) \\ y(k) = Cx(k) + v_y(k) \end{cases} \quad (10)$$

in which $v=[v_x \ v_y]$ is Gaussian multivariate white noise having zero average with covariance matrix:

$$v = \begin{bmatrix} Q_{KF} & 0 \\ 0 & R_{KF} \end{bmatrix}, Q_{KF} > 0, R_{KF} > 0 \quad (11)$$

Moreover, the initial state $x_0=x(0)$ is assumed to be a Gaussian random variable having zero average independent from v.

Under this theory, the Kalman filter in steady-state is represented by the following equations:

$$\hat{x}(k+1|k)=A\hat{x}(k|k)+Bu(k)+Md(k)$$

$$\hat{x}(k|k)=\hat{x}(k|k-1)+L(y(k)-C\hat{x}(k|k-1)) \quad (11)$$

in which $L=PC'[CPC'+R_{KF}]'$ (12)

and P is the unique positive definite solution of the algebraic Riccati equation $$P=APA'+Q_{KF}-APC'[CPC'+R]^{-1}CPA'$$

The Kalman filter is used to update the estimated insulin-glycemia state using the information concerning glucose, insulin and carbohydrates.

According to the separation principle, the estimated state is inserted in the control formula (9) in place of the real state $$u_o(k)=[1 \ 0 \ \ldots \ 0](-K_x\hat{x}(k|k)-K_d D(k)+K_{Y_o}Y_o(k)+K_{U_o}U_o(k))) \quad (14)$$

The main advantage of using a Kalman filter is that, by suitably regulating the parameters of the filter $Q_{KF}$ and $R_{KF}$, the control module 301 can be less sensitive to the noise introduced by the subcutaneous sensor 501.

Going back to the block diagram of FIG. 3, the second computing node C2 is suitable for providing the value of insulin i to be delivered to the patient P as the sum of the data $u^{MPC}$, representative of the second insulin variation value, and of the data $u_b$, representative of the basal insulin value.

Based on the block diagram of FIG. 3, the method 300 for controlling the delivery of insulin in a diabetic patient P, according to the first embodiment of the invention, is now described.

The control method 300 comprises a step of providing data d representative of at least a fraction of the foreseen meal $\hat{m}(k+i)$ that the patient will consume.

The foreseen meal $\hat{m}(k+i)$ is inserted, for example, by the patient P through a user interface (not shown in FIG. 5) with which the system 500 is equipped or it can be provided automatically by an automatic precision module.

As stated earlier, it should be repeated that in the embodiment of FIG. 3, the data d corresponds to the entire foreseen meal that the patient will consume.

The control method 300 also comprises a step of providing, by a block R representative of conventional therapy or open loop rule to which the patient P is subject, a reference insulin value $u_o$ based on the data d representative of at least a fraction of the foreseen meal $\hat{m}(k+i)$ that the patient P will consume.

The control method 300 also comprises the step of providing data representative of the difference between input data $\tilde{y}$, representative of a reference glycemic level and feedback data $y^{CGM}$, representative of the glycemic level detected in the patient P, at a previous moment k, by the subcutaneous sensor 501.

The control method 300 also comprises the step of providing, by the control module 301, based on the data representative of the difference between the input data $\tilde{y}$, representative of the reference glycemic level, and the feedback data $y^{CGM}$, representative of the glycemic level detected in the subcutaneous tissue of the patient P, and on the data d, representative of at least a fraction of the foreseen meal that the patient P will consume at the time k+i, data $u^{MPC}$ representative of a first insulin variation value.

The control method 300 also comprises the step of providing, based on the data $u^{MPC}$, representative of the first insulin variation value and on data $u_b$ representative of the basal insulin value, a value of insulin i to be delivered to the patient P.

It should be noted that the step of providing, by the control module 301, the data $u^{MPC}$, representative of a first insulin variation value, is also based on previous data representative of the first insulin variation value provided by the control module 301 in order to improve the quality of the information transmitted by the sensor to the control method of the invention.

In particular, the errors in the information transmitted by the sensor are compensated through the use, inside the control module 301, of a model of the patient system P and of a filtering module, for example a Kalman filter.

Figure 4:
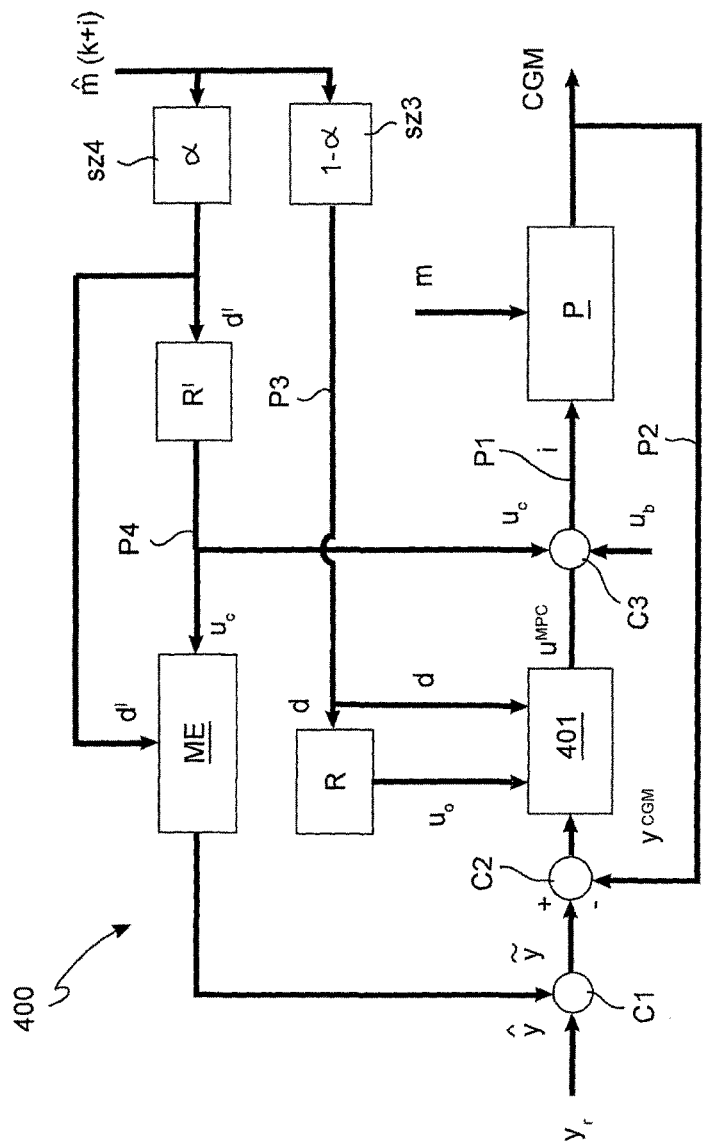
FIG. 4 schematically illustrates through a block diagram a method for controlling the delivery of insulin according to a further embodiment of the invention.

With reference now to FIG. 4, the block diagram corresponding to a method 400 for controlling the delivery of insulin, hereafter also simply control method 400, according to a second embodiment, is described.

The block diagram of FIG. 4 comprises an actuation path P1, a feedback path P2 in a closed loop, a first compensation path P3 in an open loop and a second compensation path P4 in an open loop.

It should be noted that upstream both of the first compensation path in an open loop P3 and of the second compensation path in an open loop P4 there is a respective modulation block SZ3 and SZ4, suitable for modulating the relative compensation path in an open loop as a function of a variable α.

In particular, the modulation blocks SZ3 and SZ4 are configured to continuously split the compensation of the meal into two parts, entrusting one fraction thereof (1−α) to the first compensation path in an open loop P3 and a second fraction thereof α to the second compensation path in an open loop P4.

When α=0, the modulation blocks SZ3 and SZ4 are configured to enable the first compensation path in an open loop P3 and inhibit the second compensation path in an open loop P4. In this case, the block diagram of FIG. 4 is analogous to the block diagram of FIG. 3, therefore the respective control method 400 is totally analogous to the control method 300 described earlier.

Figure 1:
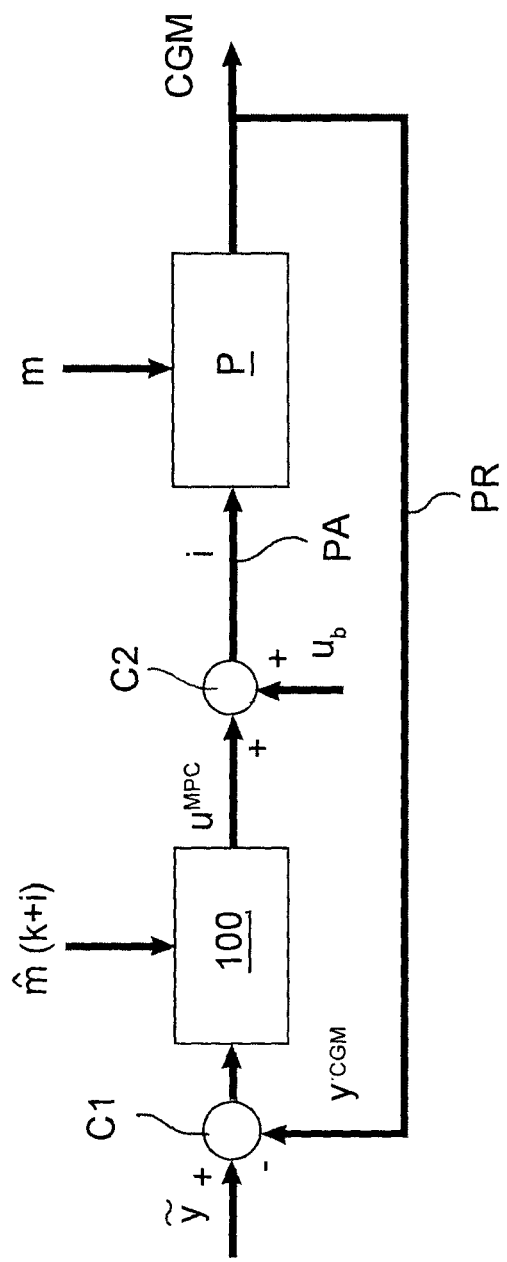
FIG. 1 schematically illustrates through a block diagram a method for controlling the delivery of insulin belonging to the prior art.
Figure 2:
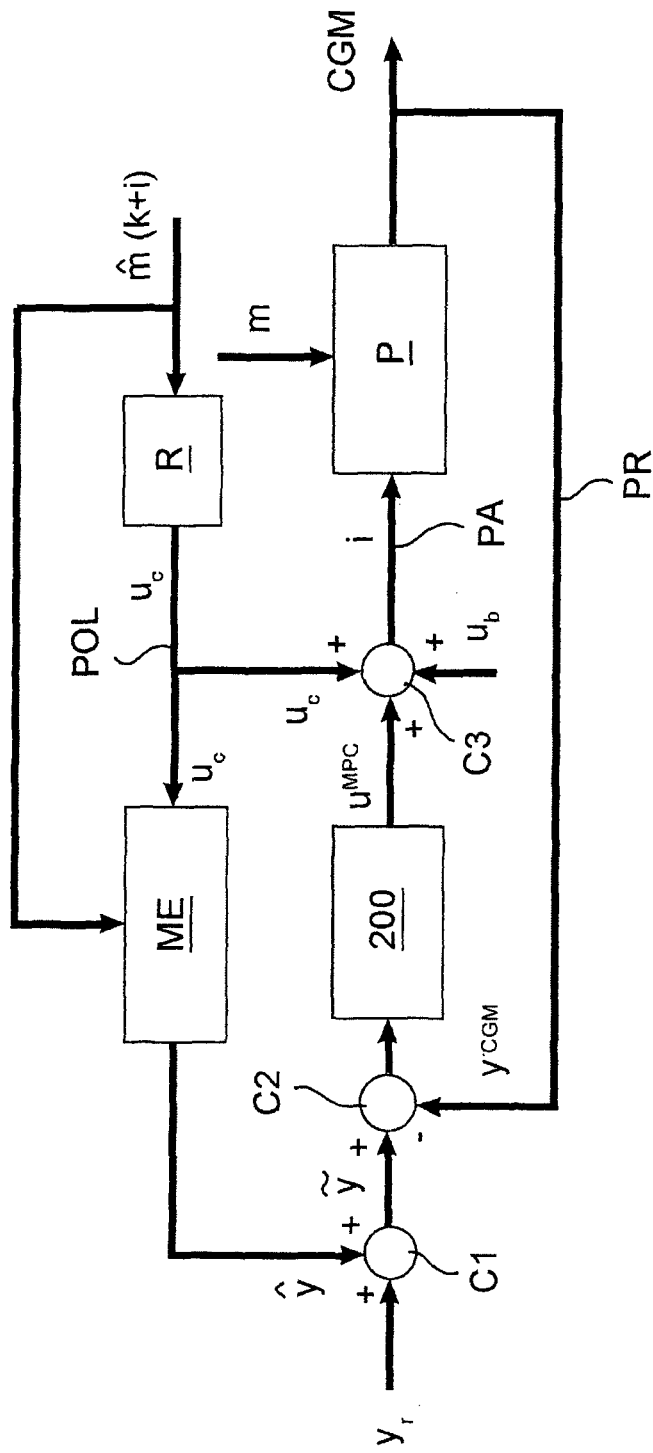
FIG. 2 schematically illustrates through a block diagram a further method for controlling the delivery of insulin belonging to the prior art.

On the other hand, when α=1, the modulation blocks SZ3 and SZ4 are configured to enable the second compensation path in an open loop P4 and inhibit the first compensation path in an open loop P3. In this case, the block diagram of FIG. 4 is analogous to the block diagram of FIG. 2, and therefore the respective control method 400 is totally analogous to the control method 200 described earlier.

In the case in which the second compensation path in an open loop P4 is enabled, the third computing node C3 is suitable for providing a value of insulin i to be delivered to the patient P as the sum of the data $u^{MPC}$ representative of the first insulin variation value, of data $u_b$ representative of the basal insulin value and of a second insulin variation value $u_c$.

It should be noted that the control method 400 based on the block diagram of FIG. 4 has greater robustness than the control methods of the prior art described earlier. Indeed, the control method 400 makes it possible to balance the compensation of the meal based on the empirical model block ME with the compensation based on the predictor model inside the block 401.

The actuation path P1 comprises a first computing node C1, a second computing node C2, a control module 401, a third computing node C3 and a block P representative of the patient-system.

The feedback path P2 in a closed loop connects the patient-system P to the second computing node C2 of the actuation path P1.

The first computing node C1 is suitable for providing the second computing node C2 with data $\tilde{y}$ representative of the reference glycemic level as the sum between data $y_r$, representative of a reference glycemic value in the absence of meals, and data $\hat{y}$, representative of a foreseen variation in glycemic level due to a further fraction of the foreseen expected meal (α$\hat{m}$(k+i)), managed by the second compensation path in an open loop P4.

The second computing node C2 is suitable for providing the control module 401, at a moment in time k+1, with data representative of the difference between the data $\tilde{y}$, representative of a reference glycemic level, and feedback data $y^{CGM}$, representative of the glycemic level detected in the patient P at a previous moment k. The feedback data $y^{CGM}$ is obtained through continuous monitoring of the glycemic level of the subcutaneous tissue of the patient P.

The first compensation path in an open loop P3 comprises a block R, representative of conventional therapy or open loop rule to which the patient P is subject, suitable for providing, based on data d representative of at least a fraction of the foreseen meal $\hat{m}(k+i)$ that the patient P will consume at the time k+i, a reference insulin value $u_o$ to the control module 401.

It should be noted that in the embodiment of FIG. 4, the data d representative of at least a fraction of the foreseen meal $\hat{m}(k+i)$ that the patient P will consume is obtained thanks to the modulation block SZ3 of coefficient $(1-\alpha)$.

It should be noted that the foreseen meal $u(k+i)$ that the patient P will consume can be provided by the patient P or by an automatic prediction module (not shown in the figures).

Moreover, the first compensation path in an open loop P3 is suitable for providing the control module 401 with the data d representative of at least a fraction $(1-\alpha)$ of the foreseen meal $\hat{m}(k+i)$ that the patient P will consume.

It should be noted that, in the embodiment of FIG. 3, the compensation of the data d is entrusted to the first compensation path in an open loop P3.

The control module 401, totally analogous to the control module 301 described earlier (for example, a linear model predictive controller LPMC), based on the data representative of the difference between the input data $\tilde{y}$, representative of the reference glycemic level, and the feedback data $y^{CGM}$, representative of the glycemic level detected in the patient P, based on data d representative of a fraction of the foreseen meal $\hat{m}(k+i)$ that the patient P will consume at time k+i and the data d representative of at least a fraction of the foreseen meal $\hat{m}(k+i)$ that the patient P will consume, is suitable for providing data $u^{MPC}$ representative of a first insulin variation value.

The third computing node C3 is suitable for providing a value of insulin i to be delivered to the patient P as the sum of the data $u^{MPC}$ representative of the first insulin variation value and of data $u_b$ representative of the basal insulin value.

The second compensation path in an open loop P4 comprises a block R', totally analogous to the block R present in the first compensation path in an open loop P3, suitable for calculating, based on data d' representative of a further fraction of the foreseen meal $\hat{m}(k+i)$ that the patient P will consume, a second insulin variation value $u_c$, calculated based on the rules used in conventional therapy, which is provided both to the third computing node C3 of the actuation path P1 and to an empirical model block ME of the second compensation path in an open loop P4.

It should be noted that in the embodiment of FIG. 4, the data d' representative of the further fraction of the foreseen meal $\hat{m}(k+i)$ that the patient P will consume is obtained thanks to the modulation block SZ4 of coefficient $\alpha$.

Moreover, it should be observed that the compensation of the data d' representative of the further fraction of the foreseen meal $\hat{m}(k+i)$ is entrusted to the second compensation path in an open loop P4.

The empirical model block ME is suitable for providing, based on the data d', representative of the further fraction of the foreseen meal $\hat{m}(k+i)$ that the patient P will consume at time k+i, and the second insulin variation value $u_c$, the data $\hat{y}$ representative of the foreseen variation in the expected glycemic level, due to the further fraction $\alpha$ of the foreseen expected meal $\hat{m}(k+i)$, to the first computing node C1 of the actuation path P1.

Based on the block diagram of FIG. 4, the method 400 for controlling the delivery of insulin in a diabetic patient P, according to the second embodiment of the invention, is now described.

The control method 400 comprises a step of providing data d representative of at least a fraction $(1-\alpha)$ of a foreseen meal $\hat{m}(k+i)$ that the patient P will consume.

The control method 400 also comprises a step of providing, by a block R representative of conventional therapy or open loop rule to which the patient P is subject, a reference insulin value $u_o$ based on the data d representative of at least a fraction $(1-\alpha)$ of a foreseen meal $\hat{m}(k+i)$ that the patient P will consume.

It should be repeated that the data $\hat{m}(k+i)$, representative of the foreseen meal, can be provided by the patient P or by an automatic prediction module.

The control method 400 also comprises the step of providing data representative of the difference between input data $\tilde{y}$, representative of a reference glycemic level, and feedback data $y^{CGM}$, representative of the glycemic level detected in the patient P, at a previous time k, by the subcutaneous sensor 501.

The control method 400 also comprises the step of providing, by the control module 401, based on the data representative of the difference between the input data $\tilde{y}$ representative of the reference glycemic level and the feedback data $y^{CGM}$ representative of the glycemic level detected in the patient P, and (ii) the data d representative of at least a fraction $(1-\alpha)$ of the foreseen meal $\hat{m}(k+i)$ that the patient P will consume, data $u^{MPC}$ representative of a first insulin variation value.

The control method 400 also comprises the step of providing, based on the data $u^{MPC}$ representative of the first insulin variation value and on data $u_b$ representative of the basal insulin value, a value of insulin i to be delivered to the patient P.

The control method 400 also comprises the step of providing the data $\tilde{y}$ representative of the reference glycemic level based on data $y_r$ representative of a reference glycemic value in the absence of meals and on data $\hat{y}$ representative of a foreseen variation in the expected glycemic level due to the data d' representative of the further fraction $\alpha$ of the foreseen meal $\hat{m}(k+i)$, managed through the second compensation path in an open loop P4.

The control method 400 comprises the step of providing, based on the data d' representative of the further fraction $\alpha$ of the foreseen meal $\hat{m}(k+i)$ that the patient P will consume at time k+i, a second insulin variation value $u_c$ for the compensation of a part of the foreseen meal.

The control method 400 also comprises a step of providing, by an empirical model block ME, based on the data d' representative of the further fraction $\alpha$ of the foreseen meal $\hat{m}(k+i)$ that the patient P will consume at time k+1 the compensation of which is entrusted to the second compensation path in an open loop P4, and the second insulin variation value $u_c$, the data $\hat{y}$, representative of the foreseen expected glycemic level due to a part of the expected meal.

The control method 400 also comprises the step of providing the value of insulin i to be delivered to the patient P based on the data $u^{MPC}$ representative of the first insulin variation value, on the data $u_b$ representative of the basal insulin value and on the second insulin variation value $u_c$.

It should be noted that the step of providing, by the control module 401, the data $u^{MPC}$ representative of a first insulin variation value is also based on previous data representative of the first insulin variation value provided by the control module 401, in order to improve the quality of the information transmitted by the sensor to the control method of the invention.

In particular, the errors in the information transmitted by the sensor are compensated through the use, inside the control module 401, of a model of the patient system P and of a filtering module, for example a Kalman filter.

Now returning in general to the control module 301 or 401 of the block diagrams of FIGS. 3 and 4, respectively, and to the description of the preferred embodiment of control module as the linear model predictive controller (LMPC), it should be observed the following.

In the control of physiological systems, two essential aspects are the intrinsic individual variability and the limited amount of information that can be collected on the individual patient-system under consideration. Therefore, the individualisation of the control module should in any case ensure the necessary flexibility without compromising simplicity and robustness of the control method.

For these reasons, in the proposed control method the control horizon N is kept at a fixed value (for example equal to 10 hours) that represents a value compatible with the time constants of the system for controlling the delivery of insulin of the invention.

The weights QKF and RKF of the Kalman filter used as predictors are also not individualised and are selected based on an analysis of simulated meal-insulin glycemic profiles.

These weights are mainly linked to the quality of the subcutaneous sensor 501 and to the Kalman filter used and less linked individually to the single patient. This means that said weights could be regulated once again in the case in which the quality of the linear model or of the subcutaneous sensor change significantly.

The method for controlling the delivery of insulin of the invention advantageously makes it possible to provide a value of insulin i to be delivered to the patient P in a more precise and reliable manner with respect to the control methods of the prior art.

Moreover, the method of the invention is able to automatically compensate for the meals of the patient thanks to the block diagrams shown in FIG. 3 and in FIG. 4 where the information available (conventional therapy, empirical model, analytical model) is exploited in the most efficient way possible.

Moreover, the second embodiment of the control method (FIG. 4) is more robust with respect to those of the described prior art.

A man skilled in the art can bring modifications, adaptations and replacements of elements with other functionally equivalent ones to the embodiments of the control method and of the related system described above, in order to satisfy contingent requirements, without departing from the scope of the following claims. Each of the characteristics described as belonging to a possible embodiment can be made independently from the other described embodiments.

The invention claimed is:

1. Method for controlling the delivery of insulin in a diabetic patient comprising steps of:
   providing data representative of at least a fraction of a meal that the patient will consume;
   providing, from a block representative of conventional therapy or open loop rule that the patient is subject to, based on the data representative of at least a fraction of the meal that the patient will consume, a reference insulin value;
   providing data representative of the difference between input data, representative of a reference glycemic level, and feedback data representative of the glycemic level detected in the patient;
   providing, from a control module, based on the data representative of the difference between the input data, representative of the reference glycemic level, and the feedback data, representative of the glycemic level detected in the patient and the data representative of at least a fraction of the meal that the patient will consume, data representative of a first insulin variation value;
   providing, based on the data, representative of the first insulin variation value, and data, representative of a basal insulin value, a value of insulin to be delivered to the patient;
   providing the data representative of the reference glycemic level based on data representative of the reference glycemic level in the absence of meals and data representative of a foreseen variation in the expected glycemic level due to data representative of a further fraction of the meal that the patient will consume;
   providing, based on the data representative of a further fraction of the meal that the patient will consume after a time interval, a second insulin variation value for compensating the data representative of a further fraction of the meal that the patient will consume;
   providing, from an empirical model block, based on the data representative of a further fraction of the meal that the patient will consume and the second insulin variation value, the data representative of the foreseen variation in expected glycemic level due to the data representative of a further fraction of the meal that the patient will consume.

2. Control method according to claim 1, also comprising the step of providing the insulin value to be delivered to the patient based on: the data representative of the first insulin variation value, the data representative of the basal insulin value, and the second insulin variation value.

3. Control method according to claim 1, wherein the control module is a predictive controller.

4. Control method according to claim 1, wherein said data representative of said at least a fraction of the meal that the patient will consume is provided by the patient or by an automatic prediction module.

5. Control method according to claim 1, wherein the step of the control module providing the data, representative of a first insulin variation value, is also based on previous data representative of the first insulin variation value provided by the control module.

6. Control method according to claim 1, wherein the data representative of at least a fraction of the meal that the patient will consume corresponds to the entire meal that the patient will consume.

* * * * *